United States Patent
Burbank et al.

(10) Patent No.: US 7,056,316 B1
(45) Date of Patent: Jun. 6, 2006

(54) VALVE PORT AND METHOD FOR VASCULAR ACCESS

(75) Inventors: Jeffrey H. Burbank, Boxford, MA (US); James M. Brugger, Newburyport, MA (US)

(73) Assignee: VASCA, Inc., Tewksbury, MA (US)

( * ) Notice: Subject to any disclaimer, the term of this patent is extended or adjusted under 35 U.S.C. 154(b) by 0 days.

(21) Appl. No.: 09/431,008

(22) Filed: Nov. 1, 1999

Related U.S. Application Data

(63) Continuation-in-part of application No. 08/942,990, filed on Oct. 2, 1997, now Pat. No. 6,007,516.

(60) Provisional application No. 60/036,124, filed on Jan. 21, 1997.

(51) Int. Cl.
*A61K 9/22* (2006.01)

(52) U.S. Cl. ............... 604/891.1; 604/288.01

(58) Field of Classification Search ............ 604/890.1, 604/891.1, 19, 48, 93.01, 164.01, 167.01, 604/167.03, 167.04, 167.06, 245, 246, 247, 604/249, 256, 288.01–288.04, 905; 251/149.6, 251/149.7, 7; 137/329.03; 261/DIG. 38
See application file for complete search history.

(56) References Cited

U.S. PATENT DOCUMENTS

| | | | |
|---|---|---|---|
| 3,998,222 A | 12/1976 | Shihata | |
| 4,181,132 A | 1/1980 | Parks | |
| 4,393,882 A * | 7/1983 | White | 422/937 |
| 4,534,759 A | 8/1985 | Trawöger | |
| 4,557,722 A | 12/1985 | Harris | |
| 4,569,675 A | 2/1986 | Prosl et al. | |
| 4,586,926 A | 5/1986 | Osborne | |
| 4,720,017 A | 1/1988 | Pestes | |
| 4,954,239 A | 9/1990 | Mueller | |
| 5,045,060 A | 9/1991 | Melsky et al. | |
| 5,053,013 A | 10/1991 | Ensminger et al. | |
| 5,057,084 A | 10/1991 | Ensminger et al. | |
| 5,067,946 A | 11/1991 | Zhadanov | |
| 5,167,638 A | 12/1992 | Felix et al. | |
| 5,180,365 A | 1/1993 | Ensminger et al. | |
| 5,226,879 A | 7/1993 | Ensminger et al. | |
| 5,263,930 A | 11/1993 | Ensminger | |
| 5,281,199 A | 1/1994 | Ensminger | |
| 5,350,360 A | 9/1994 | Ensminger | |
| 5,360,417 A | 11/1994 | Gravener et al. | |
| 5,417,656 A | 5/1995 | Ensminger et al. | |
| 5,476,451 A * | 12/1995 | Ensminger et al. | 604/175 |
| 5,476,460 A | 12/1995 | Montalvo | |
| 5,503,630 A | 4/1996 | Ensminger et al. | |
| 5,520,643 A | 5/1996 | Ensminger et al. | |
| 5,527,277 A | 6/1996 | Ensminger et al. | |
| 5,527,278 A | 6/1996 | Ensminger et al. | |
| 5,562,617 A | 10/1996 | Finch, Jr. et al. | |
| 5,637,088 A | 6/1997 | Wenner et al. | |
| 5,702,363 A * | 12/1997 | Flaherty | 604/175 |

(Continued)

FOREIGN PATENT DOCUMENTS

DE 196 03 178 5/1997

(Continued)

*Primary Examiner*—Loan H. Thanh
(74) *Attorney, Agent, or Firm*—Townsend and Townsend and Crew LLP

(57) ABSTRACT

Valved ports for accessing blood vessels and other body lumens include a lock mechanism which locks the valve fully open when a needle or other access tube is placed into the port. The lock mechanism includes a latch typically comprising one or more laterally deflectable elements, such as a pair of opposed balls. The deflected elements are pushed outwardly by the needle to engage a recess in the port which locks the valve open until the needle is removed.

10 Claims, 9 Drawing Sheets

U.S. PATENT DOCUMENTS

| | | |
|---|---|---|
| 5,741,228 A | 4/1998 | Lambrecht et al. |
| 5,755,780 A | 5/1998 | Finch, Jr. et al. |
| 5,762,805 A | 6/1998 | Truitt et al. |
| 5,810,780 A | 9/1998 | Brimhall et al. |

FOREIGN PATENT DOCUMENTS

| | | |
|---|---|---|
| EP | 0 110 117 | 6/1984 |
| EP | 0 159 260 | 10/1985 |
| WO | WO 83/02063 | 6/1983 |
| WO | WO 93/00129 | 1/1993 |
| WO | WO 94/05246 | 3/1994 |
| WO | WO 94/05351 | 3/1994 |
| WO | WO 95/19200 | 6/1995 |
| WO | WO 96/25196 | 8/1996 |
| WO | WO 96/31246 | 10/1996 |
| WO | WO 97/47338 | 12/1997 |

* cited by examiner

VALVE PORT AND METHOD FOR VASCULAR ACCESS

CROSS-REFERENCES TO RELATED APPLICATIONS

The present application is a continuation-in-part of non-provisional application Ser. No. 08/942,990, filed on Oct. 2, 1997, (now U.S. Pat. No. 6,007,516, issued Dec. 28, 1999), which claimed the benefit of provisional Application Ser. No. 60/036,124, filed on Jan. 21, 1997, the full disclosures of which are incorporated herein by reference.

BACKGROUND OF THE INVENTION

1. Field of the Invention

The present invention relates generally to the design and use of medical devices, and more particularly to the design and use of an implantable port for establishing temporary access to a patient's vascular system for hemodialysis and other extracorporeal blood treatments.

Access to a patient's vascular system can be established by a variety of temporary and permanently implanted devices. Most simply, temporary access can be provided by the direct percutaneous introduction of a needle through the patient's skin and into a blood vessel. While such a direct approach is relatively simple and suitable for applications, such as intravenous feeding, intravenous drug delivery, and other applications which are limited in time, they are not suitable for hemodialysis and other extracorporeal procedures that must be repeated periodically, often for the lifetime of the patient.

For hemodialysis and other extracorporeal treatment regimens, a variety of implantable ports have been proposed over the years. Typically, the port includes a chamber and an access region, such as a septum, where the chamber is attached to an implanted catheter which in turn is secured to a blood vessel. In the case of veins, the catheter is typically indwelling and in the case of arteries, the catheter may be attached by conventional anastomosis.

Of particular interest to the present invention, implantable ports typically include a needle-penetrable septum which permits the percutaneous penetration of a needle into the internal chamber. The chamber, in turn, is connected to one end of the catheter, and the other end of the catheter is indwelling in the blood vessel. While workable, such designs suffer from a number of problems. Repeated penetration of the septum often leads to degradation over time, presenting a substantial risk of small particulates entering the blood stream and/or need to periodically replace the port. Second, the passage of blood through the chamber or plenum will often encounter regions of turbulence or low flow, either of which can degrade the quality of blood over time.

To overcome these problems, some implantable ports have an internal valve structure which isolates the interior of the port from the lumen of the implanted catheter when the port is not in use. Such valved ports, however, have their own shortcomings. For example, self-penetrating needles often cannot be used since they will be damaged by and/or cause damage to the port. In such instances, it is frequently necessary to use a catheter combined with a removable stylet, which is both more costly and more inconvenient than use of a simple needle. Moreover, many valved ports have no means or mechanism to assure that the valve is fully opened, particularly when insertion of the access needle opens the valve. In such instances, partial insertion of the needle can result in partial opening of the valve.

Needle-actuated valved ports are described in a number of the patents listed below. For example, the ports described in U.S. Pat. Nos. 5,741,228 and 5,702,363, show a port having a duckbill valve which is opened by an elastomeric plug which is elongated by insertion of a needle. So long as the needle is fully inserted, the valve will be fully opened. It would be possible, however, to only partially insert the needle, resulting in only partial opening of the duckbill valve. Such partial opening could significantly degrade and alter the valve performance.

For these reasons, it would be desirable to provide improved valved implantable access ports for percutaneously accessing a patient's blood vessels, including both arteries and veins. The access ports will comprise a valve structure for isolating the port from an associated implanted catheter when the port is not in use. The valve will preferably provide little or no structure within the blood flow lumen of the access port and will even more preferably not require passage of a needle or other access tube through the seating portion of a valve in order to open the valve. Furthermore, the port structure including the valve elements therein will have a substantially uniform cross-sectional area and will present no significant constrictions or enlargements to disturb fluid flow therethrough. Preferably, the port designs will permit percutaneous access using a conventional needle, such as a fistula needle, without damage to either the port or the needle. Still more preferably, the ports will include means for locking the valve structures open in response to insertion of the needle or other access device. Ports and valves according to the present invention will meet at least some of these objectives.

2. Description of the Background Art

U.S. Pat. No. 5,562,617 and WO 95/19200, assigned to the assignee of the present application, describe implantable vascular access systems comprising an access port having an internal slit or duckbill valve for preventing back flow into the port. Vascular access ports having various valves for isolating the port from the vascular system in the absence of external percutaneous connection to the port are described in the following U.S. Pat. Nos. 5,954,691; 5,741,228; 5,702, 363; 5,527,278; 5,527,277; 5,520,643; 5,503,630; 5,476, 451; 5,417,656; 5,350,360; 5,281,199; 5,263,930; 5,226, 879; 5,180,365; 5,057,084; and 5,053,013. Other patents and published applications which show implantable ports having valve structures opened by insertion of a needle include U.S. Pat. Nos. 4,569,675; 4,534,759; 4,181,132; 3,998,222; and WO 96/31246. U.S. Pat. No. 5,637,088 describes a septum-type implantable port which employs a dual needle to help prevent dislodgment.

SUMMARY OF THE INVENTION

The present invention provides devices and methods for percutaneously accessing a body lumen through an implanted access port. More particularly, the present invention provides methods and devices for locking open a valve assembly within an access port by the act of inserting the access tube. Insertion may involve simply advancing the access tube in the forward direction, or it may involve additional or alternative movements such as rotation. Reversal of the needle movement and/or removal of the access tube will in turn release the lock and close the valve assembly. The present invention provides a "positive" locking action and reduces any variability in access, such as a "half-opened" valve, and reduces the risk of blood loss due to valve closure during fluid transfers.

The implantable access ports for use with the present invention are preferably capable of high volume withdrawal and/or return of blood or other fluids, particularly for patients undergoing an extracorporeal blood therapy, such as hemodialysis, hemofiltration, hemodiafiltration, apheresis, or the like. The vascular access ports allow for high volumetric rates of blood or other fluid flow therethrough, typically allowing for rates above 250 ml/min, usually above 300 ml/min, preferably at least 400 ml/min, and often 500 ml/min or higher, using a single needle or other access device. Such high volumetric flow rates are quite advantageous in reducing the time required for performing the extracorporeal blood treatment, particularly for otherwise lengthy treatments which require large total volumes of treated blood, such as hemofiltration. To ensure high flow rates and minimum time requirements, it is useful to know that the valve is completely open, allowing full access to the body lumen through the conduit while the access tube is in place. Likewise, it is beneficial to know that the valve is completely closed when the access tube is removed, either by careful disengagement or by accidental pull-out, since such high flow rates will cause a significant amount of fluid to be lost if the valve is unknowingly left open.

According to a first aspect of the method of the present invention, a body lumen in the patient may be accessed by percutaneously inserting an access tube into an implanted access port. The access tube may be percutaneously inserted into the access port so that the access tube engages a valve lock having a latch which opens a valve structure within the port or the conduit. Alternatively, the latch may open the valve structure as a result of rotational or other movement of the access tube during or subsequent to insertion. The valve structure is located remotely from that portion of the access port into which the access tube has been inserted and may be present in the conduit itself or in a separate assembly within the port. The latch may be mechanical or hydraulic, usually being mechanically coupled to a spring-loaded valve assembly or a spring-loaded plunger assembly which mechanically opens a valve. Alternatively, a hydraulic latch could be provided where a pushing force on a plunger assembly is hydraulically actuated or a valve opened by insertion of the access tube.

In a more particular aspect of the present invention, an implantable port comprises a base having a passage for receiving an access tube. A valve assembly is disposed in the base and includes a bore which is aligned with the passage in the base and which also receives the access tube. The valve assembly is locked by action of a latch which shifts position to lock the valve assembly open in response to movement of the access tube. The latch is disposed between the passage in the base and the bore in the valve. The latch typically comprises at least one space-filling element. One or a number of these elements are displaced into one or more receptacles adjacent to the passage by movement of the access tube in the passage, wherein the presence of the space-filling elements, typically opposed balls, in the receptacle locks the valve open. When the valve is opened by action of a plunger, such as a plunger protruding through a duckbill or miter valve, the balls or other space-filling elements move downward and outward to depress the plunger and lock the plunger open.

The space-filling elements of the latch typically comprise a pair of balls, usually opposed stainless steel balls similar to small ball bearings, disposed between the passage in the base and the bore in the valve. In valve assemblies that open and close with the action of a spring-loaded plunger, the balls are spring-biased to close against one another between the passage and the bore in the valve assembly. In one embodiment, the insertion of the access tube through the passage forces the balls apart and the access tube passes into the bore of the valve assembly. As the balls move apart (outward), they also move downward into receptacles. This movement is directed by interior walls sloping outward between the passage and the bore. Such action depresses the plunger, which opens the valve. While the access tube is inserted, the balls are held against the tube and in the receptacles by the spring-loaded plunger and the angled interior walls. Not only does this lock the valve open, but the static friction of the balls against the tube may help to hold the access tube in the passage. Interior walls with an angle of 50 degrees or greater (relative to a lateral plane through the port) have been found to provide higher frictional forces for needle retention. Removal of the tube allows the balls to move out of the receptacles in an upward direction, by action of the spring-loaded plunger, and an inward motion directed by the angled interior walls so that they are again in contact in the passage. In alternative embodiments, insertion of the access tube may be coupled with a rotational movement of the access tube. Such rotational motion would force the balls apart and facilitate the movement of the balls into the receptacles, thus opening the valve. Reversal of such movement by the access tube and/or removal of the access tube subsequently closes the valve.

In a second aspect of the method of the present invention, percutaneous access to a patient's blood vessel is provided by maintaining a conduit between an implanted access port and the blood vessel. An access tube is percutaneously inserted into a tube seat within the access port to establish a generally fluid tight seal therein. When inserted, the access tube actuates a valve lock to open a valve structure to permit flow through the conduit. The valve structure will usually be internal to the port but, in some cases, could be located outside of the port itself. Preferably, the tube seat comprises a tapered bore within the access port which frictionally engages the outside access tube as the tube is inserted into the bore. More preferably, insertion of the access tube into the tube seat depresses the tube seat relative to a base of the access port in order to actuate the valve lock which opens the conduit. The valve lock may take a variety of forms, including latch motions as described above.

The tube seat will remain locked in its depressed condition until the access tube is removed from the base. By forming the tube seat from (or lining the tube seat with) a hard material, preferably a material harder than the needle or other access device which is to be used, the likelihood of damage to the valve can be greatly reduced. Moreover, the tapered tube seat design is not prone to damaging needles when they are inserted into the port. Thus, the port of the present invention is particularly suited for use with self-penetrating, sharpened needles, such as fistula needles, unlike many ports of the prior art.

A further understanding of the nature and advantages of the invention will become apparent by reference to the remaining portions of the specifications and drawings.

DESCRIPTION OF THE SPECIFIC EMBODIMENTS

Figure 1:
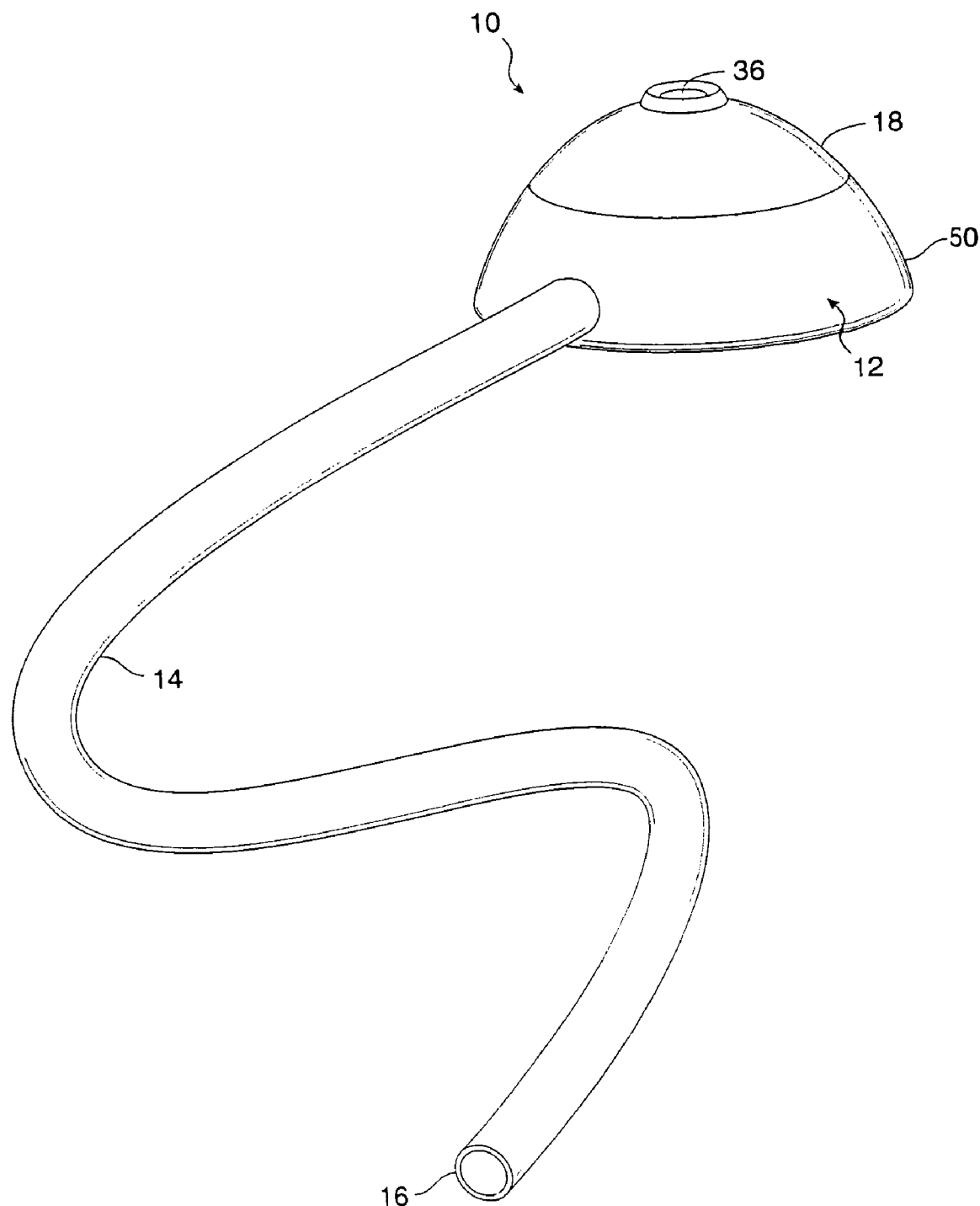
FIG. 1 is a perspective view of an access port having a flexible conduit extending therefrom constructed in accordance with the principles of the present invention.

The present invention provides methods and apparatus for facilitating percutaneous access to a body lumen of a patient. Exemplary body lumens, include blood vessels, the peritoneal cavity, and the like. The methods are particularly useful for accessing blood vessels, including both arterial blood vessels and venous blood vessels. While the remaining description is directed particularly at blood vessels, it will be appreciated that the invention applies to all body lumens and cavities where selective percutaneous access might be desired. For example, the ports can be used for introduction and removal of dialysate in peritoneal dialysis procedures. Access ports according to the present invention are implanted subcutaneously so that a passage therein lies a short distance beneath the surface of the patient's skin, typically being within 3 mm to 20 mm of the skin's surface. An access tube may then be percutaneously inserted into the passage in the access port in order to provide communication with the blood vessel or other body lumen via the access port. Such access can be provided for a variety of purposes, usually involving withdrawal of blood, the extracorporeal treatment of the withdrawn blood, and/or the return of the treated blood to the patient. Such extracorporeal blood treatment will most often be for hemodialysis, but can also be for hemofiltration, hemodiafiltration, apheresis, and the like. In addition to extracorporeal treatment, the access port of the present invention can be used for perfusing drugs, fluids, and other materials directly into a patient's circulation for a variety of purposes.

The present invention relies on implantation of the access port and connection of the port to the target blood vessel or other body lumen via a conduit, which is regulated by a valve. The valve is opened by movement of an access tube in the port, and closed by reversal of the movement, such movement may involve simply inserting the access tube or it may involve rotational motion or the like. When motion is applied, the access tube will engage a valve lock having a latch which shifts position to lock the valve assembly open. Locking the valve open ensures both that the valve is completely open and that the valve remains open to prevent accidental closure. When the tube is removed, the latch will shift back to its previous position and unlock and the valve, both ensuring that the valve is completely closed and avoiding the possibility of accidental leakage.

The access tube will usually be a needle which can be directly pierced (percutaneously introduced) through the patient's skin and into the implanted port. Thus, the needle will usually have a sharpened tip in order to permit it to be self-introduced through the skin. Of course, access tubes having blunt distal ends could be used by first piercing the skin with a separate blade, stylet, needle, or the like, and thereafter introducing the access tube into the resulting incision or hole. The access tube could also be introduced using an internal stylet which is subsequently withdrawn, leaving the tube in place in the port. While the port of the present invention can accept a wide variety of different access tubes, it is significant that it can be used with standard hypodermic needles, standard fistula needles, large fistula needles, e.g. 16 gauge, 14 gauge, or larger, and the like. Prior port designs which employ a septum require the use of relatively small non-coring Huber needles or the use of a combination tube/stylet in order to avoid significant damage to the septum. The same is true of ports which employ slit valves through which a tube must pass, such as many of the Ensminger designs described above. In all cases, the needle or other access tube will be rigid and possess sufficient column strength in order to actuate a linkage for relieving clamping of the conduit, as described in more detail below.

The port of the present invention is also advantageous since it will not generally be damaged by use of an inappropriately sized needle or other access tube. While most prior art ports can be damaged through use of the wrong type or size of needle, the port of the present invention will not be damaged by larger needles (which simply engage the access aperture and do not pass into the port) or by smaller needles (which enter the access aperture but pass harmlessly into the interior of the base). In particular, the passage in the access port which receives the needle or other access tube may have at least one bend, usually a 90° elbow, which presents a surface which is engaged by a smaller needle. By forming or backing the passage from a material which is harder than the needle, e.g. a stainless steel, the port will be protected from any damage from improper insertion of a small needle.

An exemplary access port 10 comprising a base 12 and flexible conduit 14 is illustrated in FIGS. 1, 2, 2A, 3, and 3A. As shown in FIG. 1, the flexible conduit 14 extends from the base 12 and terminates at a distal end 16 which is suitable for direct anastomosis (suturing) to a blood vessel. Suitable conduit structures are described in U.S. Pat. No. 5,562,617, the full disclosure of which is incorporated herein by reference. Exemplary conduit structures may be composed of silicone rubber.

Figure 2:
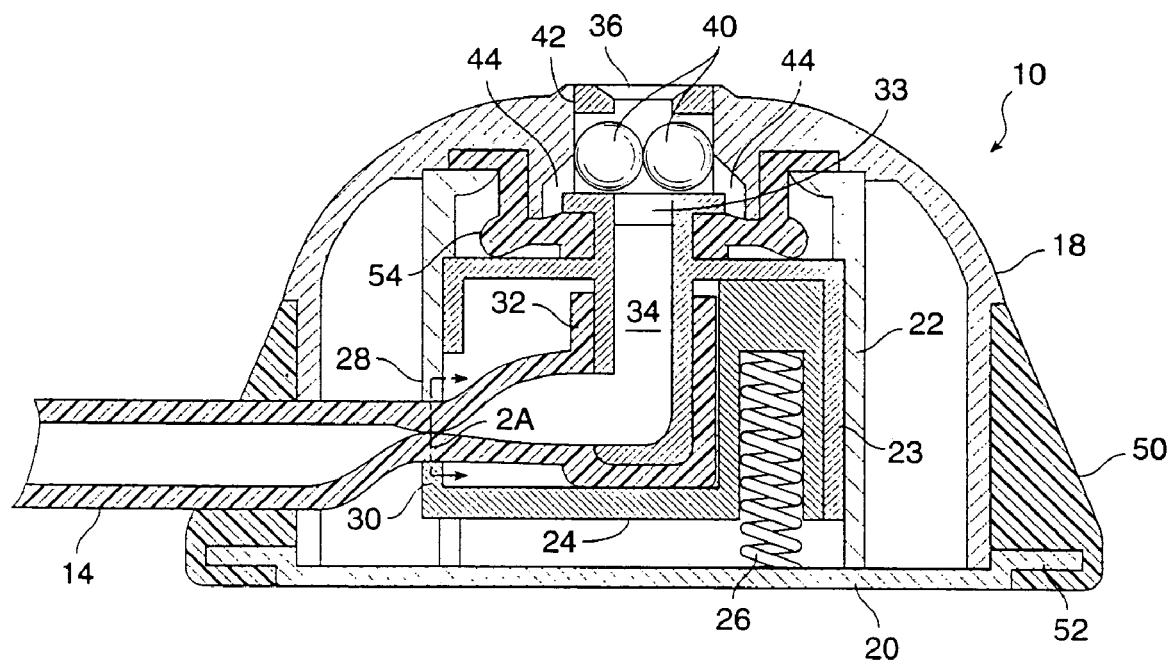
FIG. 2 is a side, cross-sectional view of the access port of FIG. 1 shown with a closed internal clamp structure.
Figure 2A:
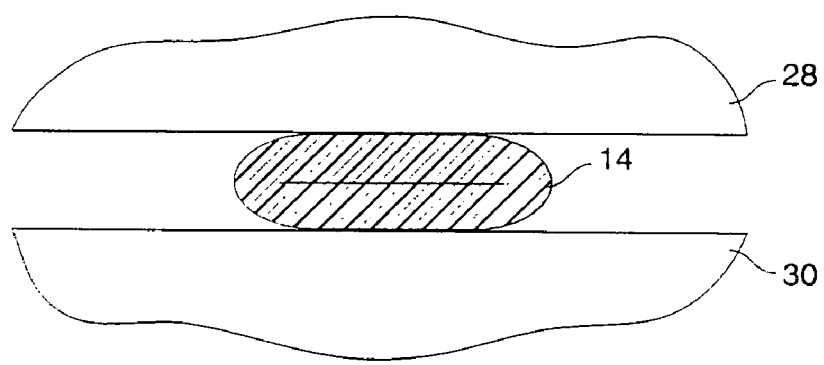
FIG. 2A is a partial cross-sectional view taken along line 2A—2A of FIG. 2.
Figure 3:
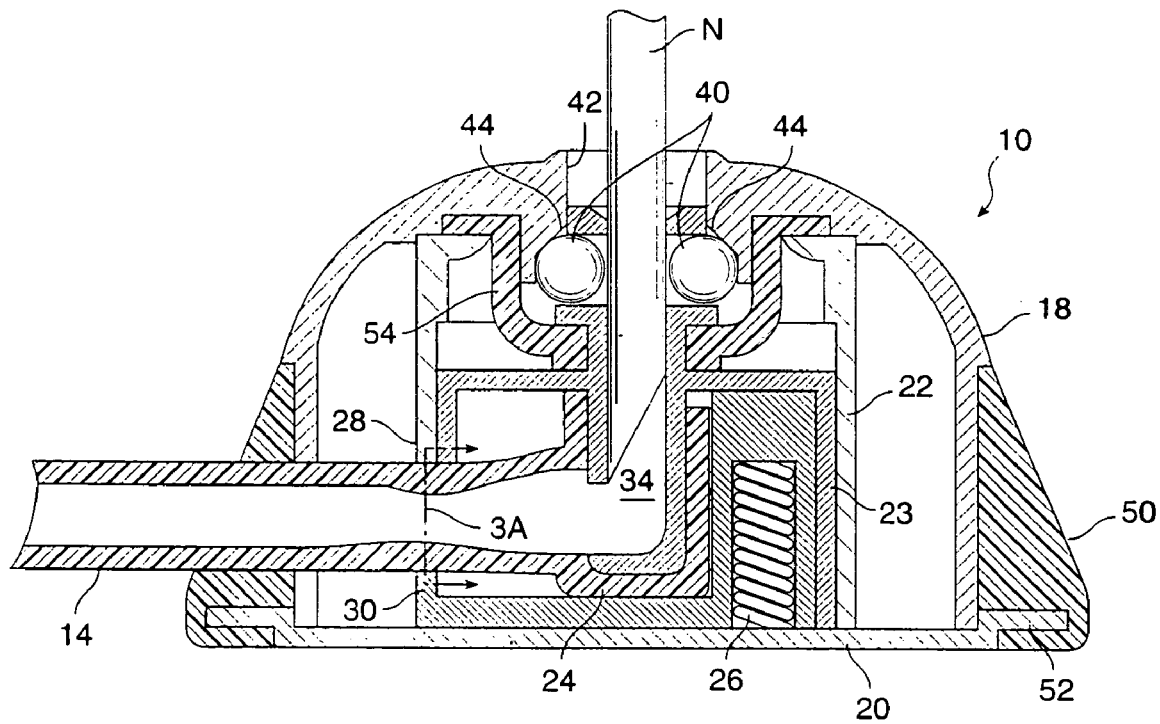
FIG. 3 is a side, cross-sectional view of the access port of FIG. 1 as shown with the internal clamp structure opened in response to the insertion of an access needle.
Figure 3A:
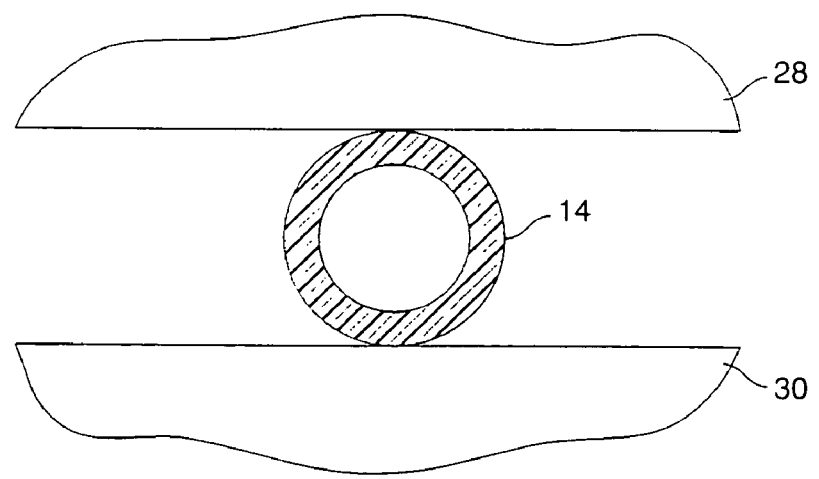
FIG. 3A is a partial cross-sectional view taken along line 3A—3A of FIG. 3.
Figure 3B:
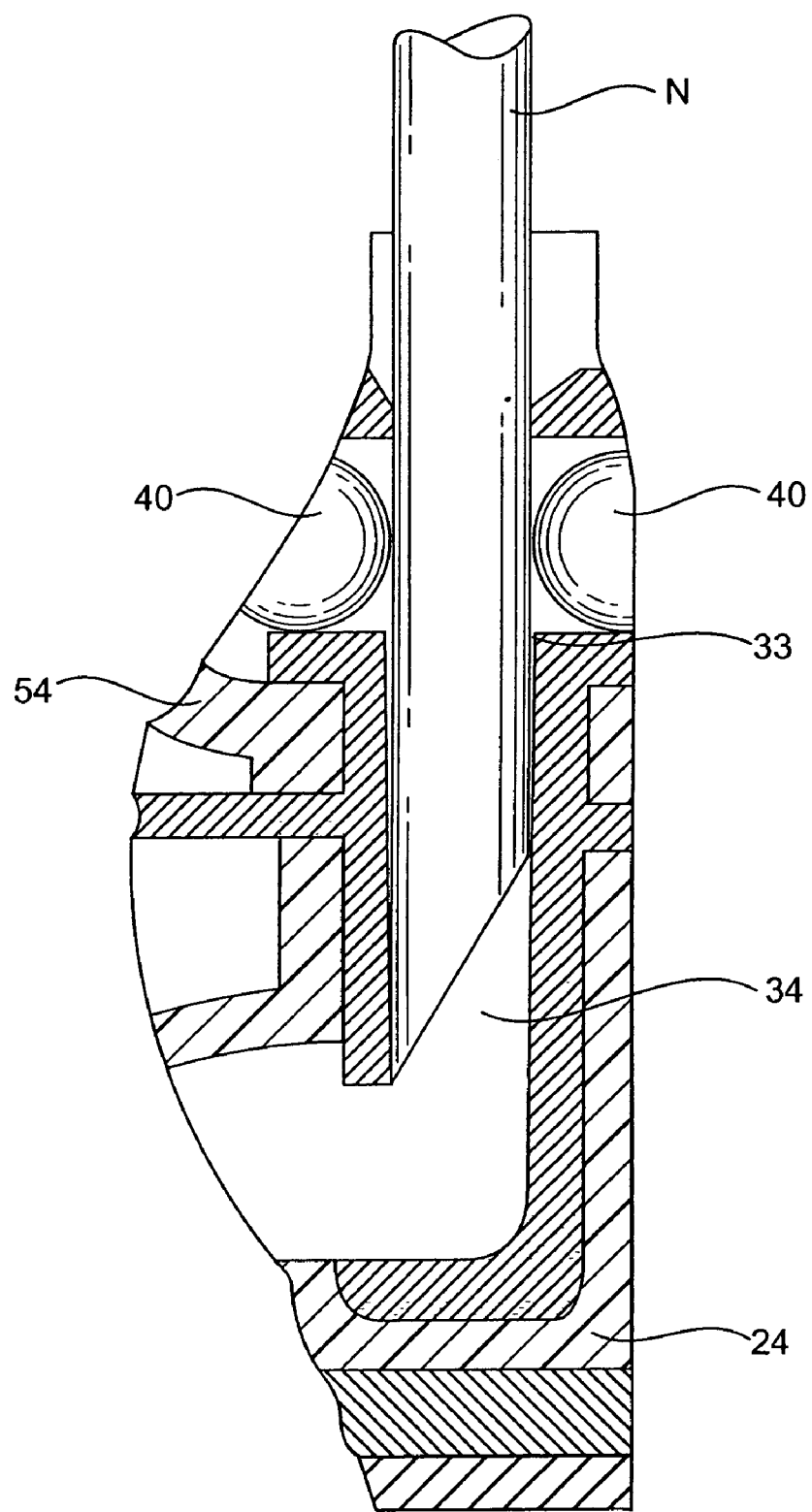
FIG. 3B is a detailed, cross-sectional view illustrating the taper of a needle when inserted into the port of FIG. 3.

The base 12 of access port 10 comprises an upper shell 18, a base plate 20, an internal cylinder 22, and a vertically reciprocating plunger 23 disposed within an actuator block 24, where the assembly of the plunger and actuator block are together disposed within the cylinder 22. As shown in FIGS. 2 and 2A, a spring 26 urges the plunger 23 and actuator block 24 upwardly relative to the base 20. When the plunger 23 and actuator block 24 are in their upward position, the conduit 14 is pinched closed between an upper lip 28 which is a portion of the wall of cylinder 22 and a lower lip 30 which is portion of the actuator block 24. A proximal end of the conduit 14 is connected to the lower end of a tube 32 which depends into an interior volume of the actuator block 24. The depending tube 32 provides an axial bore 34 for receiving a needle N, as illustrated in FIGS. 3 and 3A. A tapered region 33 is formed near the upper end of axial bore 34 and is sized to engage and seal against the outer side wall of a needle or other access tube which is introduced into the bore, as best seen in FIG. 3B.

The needle N is introduced through an opening 36 at the upper end of the axial bore 34. Typically, though not necessarily, the opening 36 has a slight chamfer (conical shape) which allows the needle N to be introduced into the bore 34. A pair of balls 40 are disposed in an upper portion of the tube 32 and contained within a circular aperture 42 in the shell 18 on the actuator block 24 as in its raised configuration, as shown in FIG. 2. When needle N is introduced through the opening 36, it will encounter the balls 40 and depress the plunger 23 and the actuator block 24 downward until the block reaches its lower configuration, as shown in FIG. 3. At that time, the balls 40 will move radially outward into an expanded portion or ramp 44 of the aperture 42. The balls 40 will thus become locked within the expanded portion or ramp 44, holding the actuator block 24 in its lowered position, so long as the needle N remains in place.

When the actuator block 24 has been lowered, as shown FIGS. 3 and 3A, the opposed lips 28 and 30 are opened in order to relieve external clamping on the conduit 14. Thus, as the needle N is inserted into the access port 10, the clamping mechanism which has previously closed the flexible conduit 14 will be opened. When the needle N is removed, the spring 26 will urge the actuator block 24 upwardly, and the access port will return to the configuration shown in FIGS. 2 and 2A.

Conveniently, a silicone overmolding 50 is provided around the base of the access port 10 in order to facilitate implantation of the access port. A flange 52 extending radially outwardly from the base plate 20 will include holes (not illustrated) for suturing into tissue. The inclusion of the silicone overmolding 50 will prevent tissue ingrowth into the holes. Preferably, a silicone seal 54 will be provided between an internal surface of the upper shell 18 and an upper portion of the tube 32. The silicone seal 54 prevents the intrusion of blood or other fluids from surrounding tissue and/or which may leak from the needle N into the interior of the access port 10.

In a preferred aspect of the access port 10 of the present invention, the axial bore 34 will be tapered in the downward direction, as best seen in FIG. 3B, over region 33. The size of the bore and degree of the taper will be selected to frictionally engage conventional needles or other access tubes so that a tight seal is formed as the access tubes are inserted into the axial bore 34. The taper also provides a stop so that the needle N will not penetrate into the horizontal lumen defined by the conduit 14.

It can thus be seen that the combination of needle, access port 10, and flexible conduit 14 provides a substantially continuous and smooth flow path for fluids from and/or to the patient's vascular system. In particular, the use of external clamping for closing flow through the conduit 14 eliminates the need for an internal valve structure within the conduit or elsewhere within the access port to define a valve seat, i.e. that portion of the valve which closes to inhibit flow therethrough. The particular linkage shown for relieving clamping from the flexible conduit is simple, reliable, and relatively inexpensive to produce. Very few moving parts are needed, yet a positive seal is reliably achieved every time the needle N is withdrawn from the access port 10. Moreover, once the needle N is introduced into the access port 10, the clamp mechanism is locked in its open configuration to assure that full flow through the lumen of the flexible tube and other portions of the access port are maintained.

Figure 4A:
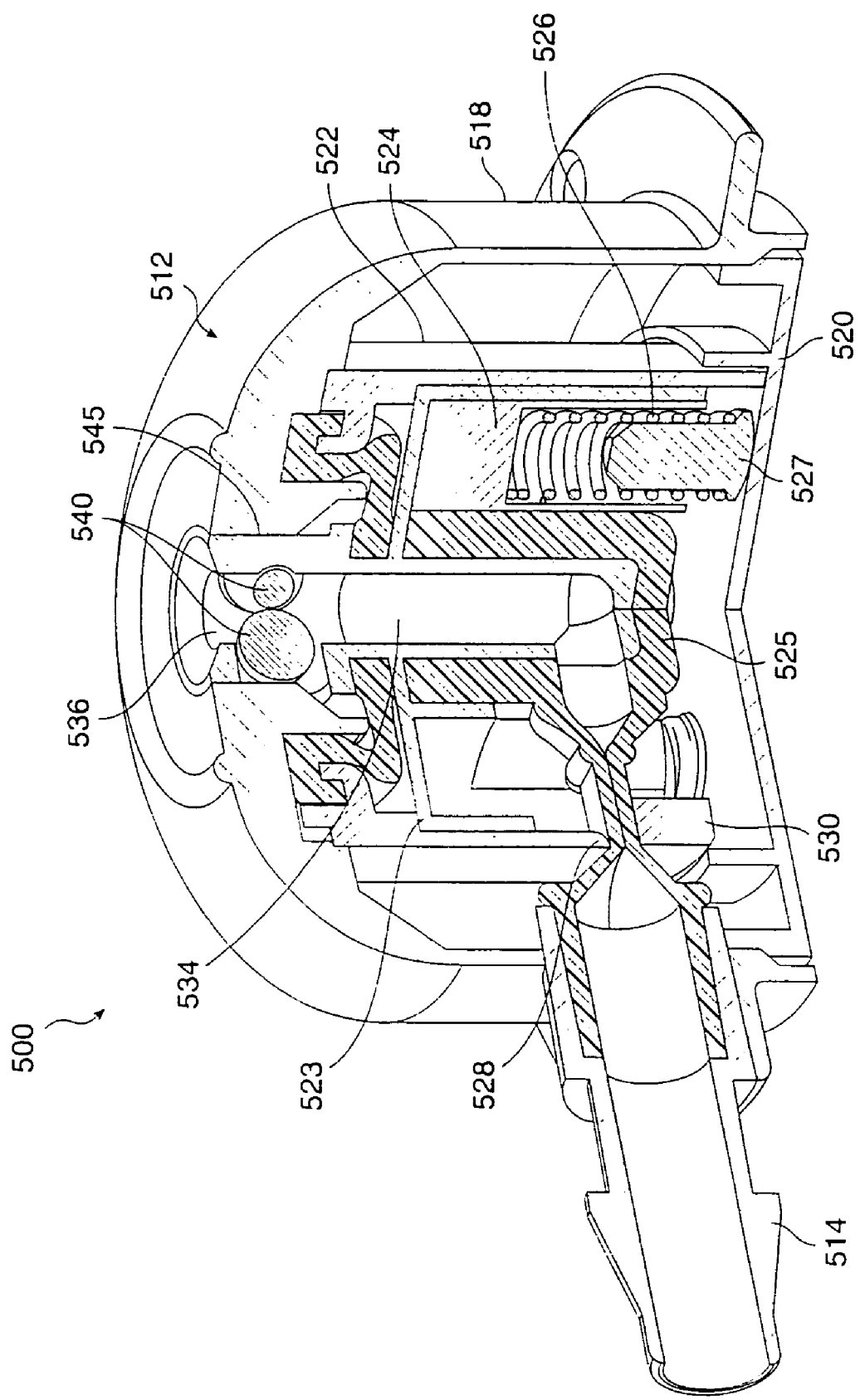
FIGS. 4A and 4B illustrate an alternative pinch tube connection design.
Figure 4B:
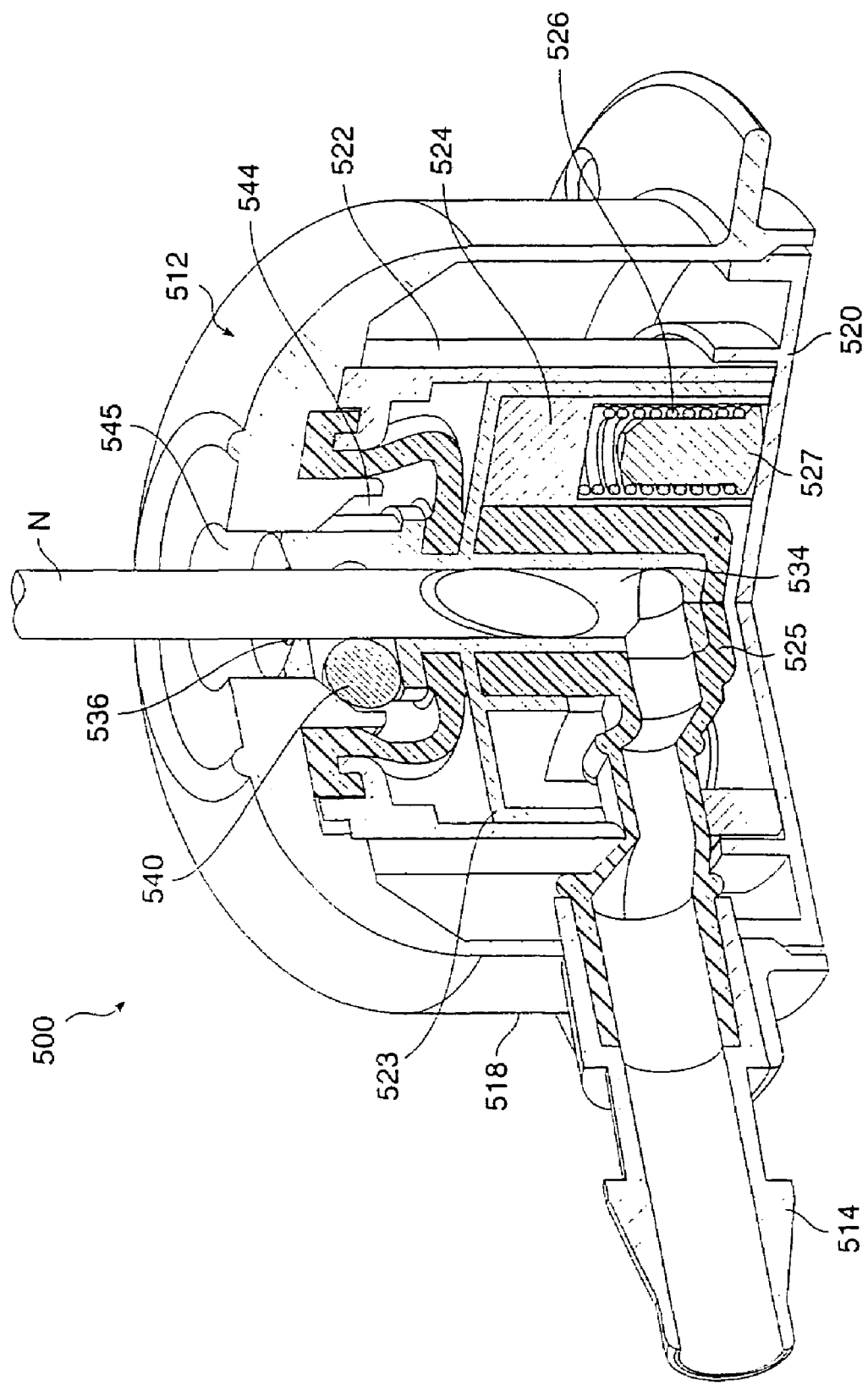

Referring now to FIGS. 4A and 4B, an additional embodiment of an access port 500 constructed in accordance with the principles of the present invention includes a body 512 having a nipple 514 extending laterally outward from the body 512. The nipple 514 is suitable for connection to a flexible conduit (not shown). The body 512 includes an upper shell 518, a base plate 520, an internal cylinder 522, a vertically reciprocating plunger 523 and an actuator block 524. The plunger 523/actuator block 524 as shown in their vertically raised position in FIG. 4A and its vertically depressed or lowered configuration in FIG. 4B.

Since the conduit does not extend into the base 512, the port embodiment 500 of FIGS. 4A and 4B employs a separate pinch tube 525, where the pinch tube is pinched closed between an upper lip 528 which is part of the cylinder 522 and a lower lip 530 which is part of the reciprocating actuator block 524. When the actuator block 524 is lowered, as shown in FIG. 4B, the external clamping of the pinch tube 525 is relieved.

The actuator block 524 is urged upwardly by spring 526 which is mounted over a pin 527, and the plunger 523 comprises an axial bore 534 for receiving a needle N, as shown in FIG. 4B. The needle N passes through aperture 536 and into the passage 534 in the plunger 523. As the needle enters the passage 534, it passes through opposed balls 540 which first cause lowering of the plunger 523 and the actuator block 524 and then are captured in an expanded portion or ramp 544 of the passage 545, as illustrated in FIG. 4B.

While the entry of needle N into the passage 534 and through opposed balls 540 may be effected simply by inserting the needle vertically downward, once the needle is fully lowered, and engaged by the tapered wall of passage 534 (as shown in FIG. 4B), the valve is "locked" open by the balls 540. The needle is held in place by friction fit in the tapered region of the passage 534. In addition, the static friction of the balls against the tube may help to hold the access tube in the passage. Such retention protects the patient against accidental loss of the needle. It has been found that simple removal techniques allow the needle to be pulled from the port without significant hindrance. Thus, the combination of opposed balls 540 and the expanded portion 544 for capturing the balls not only locks the valve open, it also secures the needle in place until it is desired to remove the needle.

Figure 5A:
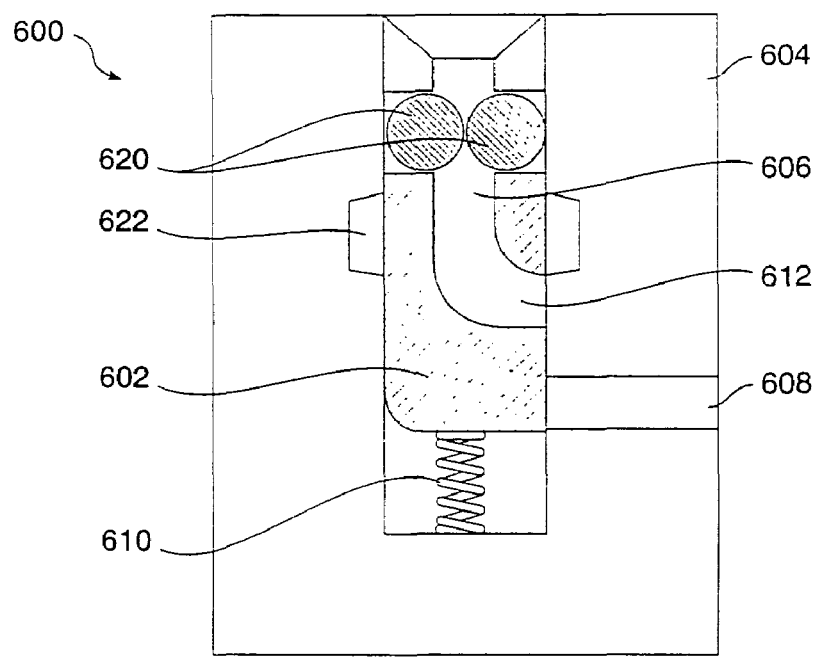
FIGS. 5A and 5B illustrate a slide valve embodiment of the implantable port of the present invention.
Figure 5B:
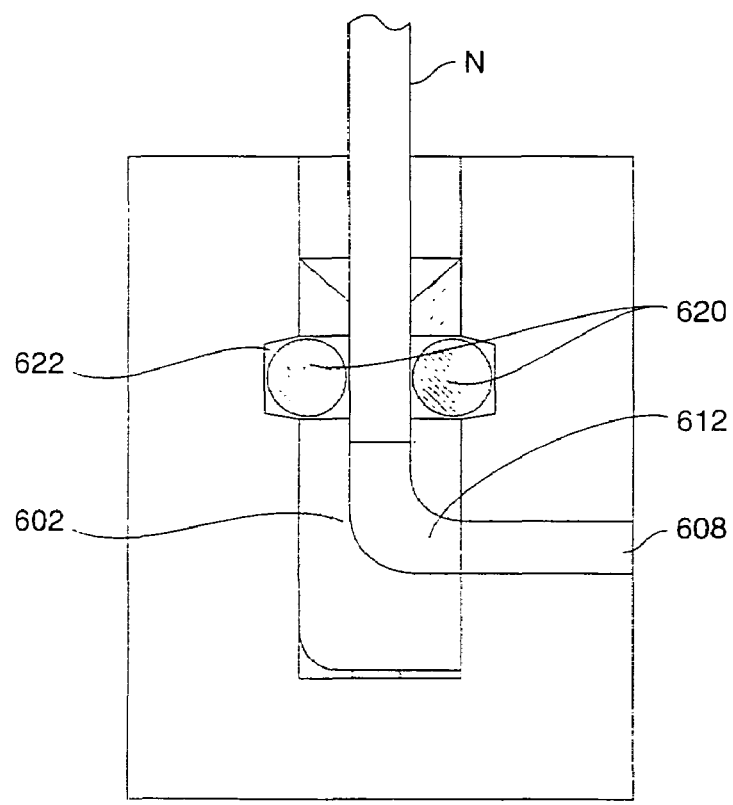

Referring now to FIGS. 5A and 5B, an alternative valve structure for use in the implantable ports of the present invention is illustrated. Instead of employing a pinch valve, as previously described, the ports may employ a sliding valve 600 or a reciprocating block 602 is formed within the base enclosure 604 (only a portion of which is illustrated). The reciprocating block 602 defines an inlet portion 606 of a passage through the port. An outlet portion 608 of the passage is also provided in the port. Initially, when no needle is present a spring 610 urges the reciprocating block 602 upward so that a side portion 612 of the passage is out of alignment with the outlet portion 608. Thus, the sliding valve structure 600 is closed. By introducing a needle N or other access tube into the valve structure 600, the reciprocating block 602 is lowered so that the side branch 612 of the passage comes into alignment with the outlet portion 608, as illustrated in FIG. 5B. The valve is thus open. The valve can be held in the open position by a pair of opposed balls 620 which are received in an enlarged recess 622, generally as described above in connection with the previous embodiments.

Figure 6A:
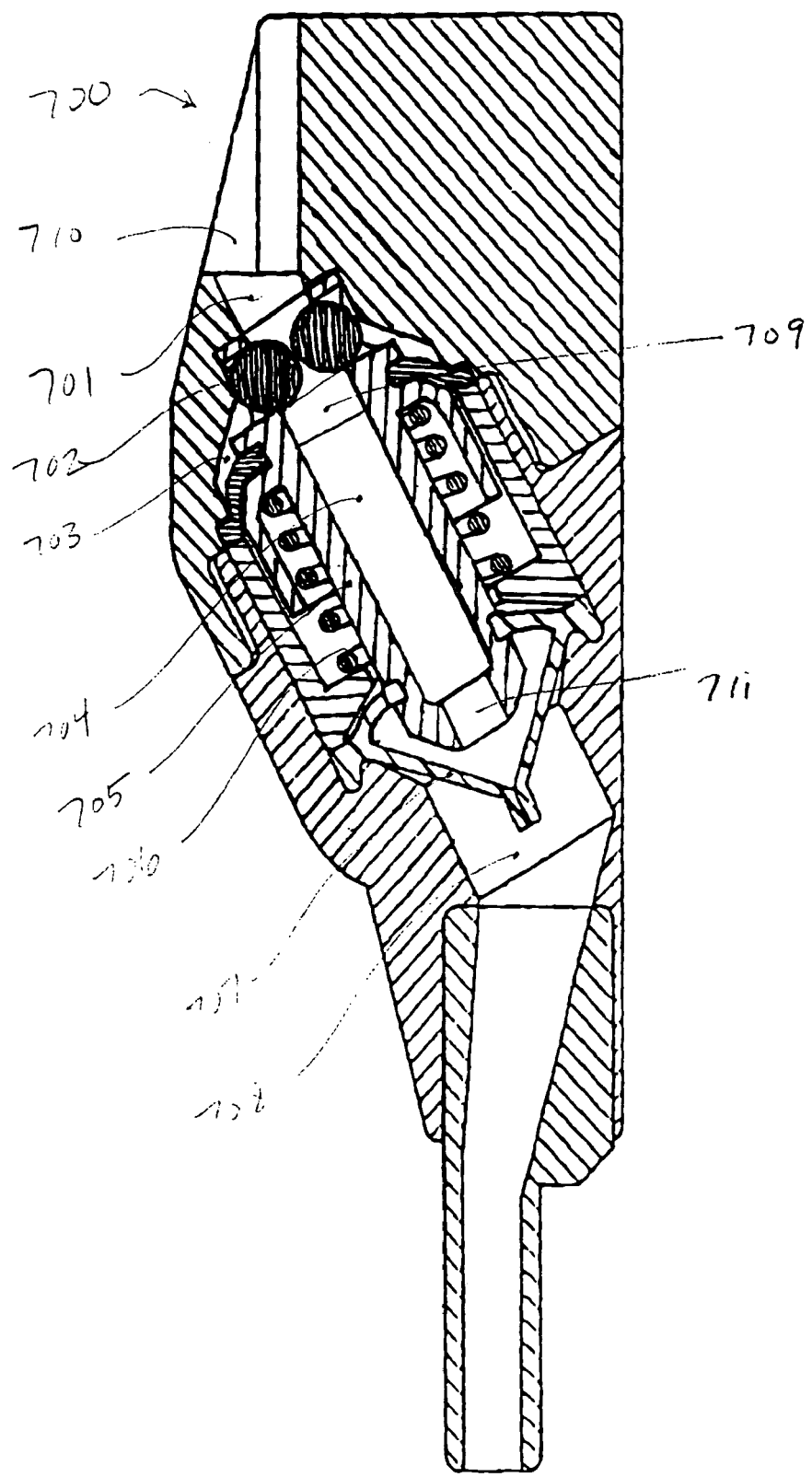
FIGS. 6A and 6B illustrate an access port having a valve lock mechanism which functions with a duckbill valve.
Figure 6B:
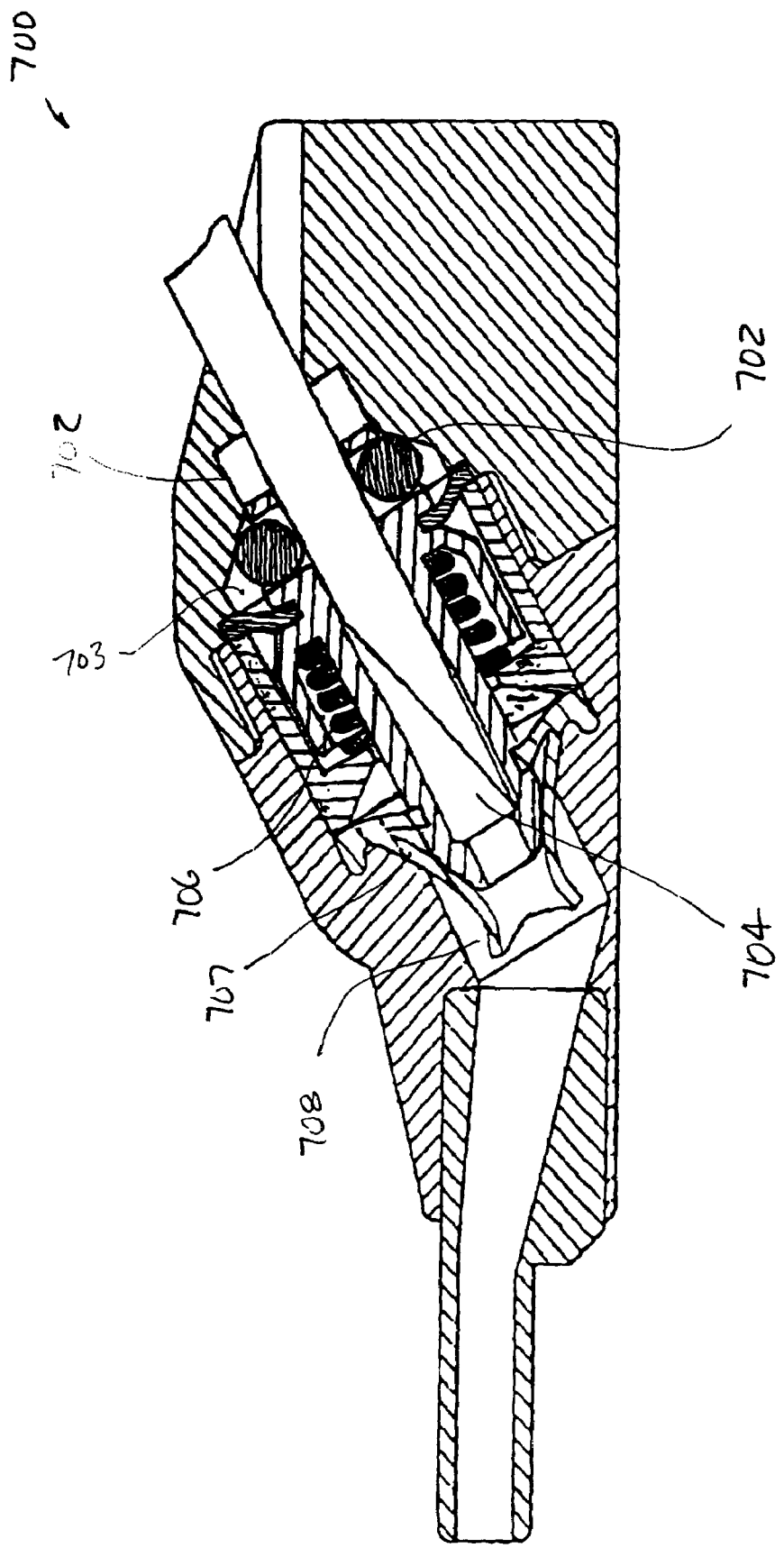

Referring now to FIGS. 6A and 6B, an alternative valve structure for use in the implantable ports of the present invention is illustrated. Instead of employing a pinch valve or sliding valve, as previously described, a port may employ a duckbill or miter valve. An exemplary port 700 having duckbill valve assembly comprises a base having a passage 701, balls 702, a receptacle or ramp 703, an axial bore 704, a vertically reciprocating plunger 705, and a duckbill valve 707. A spring 706 urges the plunger 705 upwardly relative to the duckbill valve 707. When the plunger 705 is in its upward position, the duckbill valve 707 is closed and the conduit 708 is not accessible. A tapered region 709 is formed near the upper end of the axial bore 704 and is sized to engage and seal against the outer side wall of a needle or other access tube which is introduced into the bore 704.

A needle N is introduced through an opening 710 at the upper end of the axial bore 704. Typically, though not necessarily, the opening 710 has a slight chamfer (conical shape) which allows the needle N to be introduced into the bore 704. A pair of balls 702 is disposed in the passage 701 and held in position by the plunger 705 in its raised configuration, as shown in FIG. 6A. When needle N is introduced through the opening 710, it will encounter the balls 702, urging the balls forwardly to engage and depress the plunger 705 downward until the plunger 705 reaches its lower configuration where the duckbill valve 707 is opened, as shown in FIG. 6B. At that time, the balls 702 move radially outward into a receptacle 703. The balls 702 thus become locked within the receptacle 703, holding the plunger 705 in its lowered position, so long as the needle N remains in place.

In a preferred aspect of the access port 700 of the present invention, the axial bore 704 will be tapered in the downward direction. The size of the bore and degree of the taper will be selected to frictionally engage conventional needles or other access tubes so that a tight seal is formed as the access tubes are inserted into the axial bore 704. The taper also provides a stop so that the needle N will not penetrate the end of the plunger 705. In a further preferred aspect of the access port 700 of the present invention, the plunger assembly 705 will comprise an end cap 711 affixed to its end. The cap 711 will be adapted to withstand repeat contact with the access tube, resisting passage of the tube such that the tube will not penetrate or damage the valve 707.

Although the foregoing invention has been described in some detail by way of illustration and example, for purposes of clarity of understanding, it will be obvious that certain changes and modifications may be practiced within the scope of the appended claims.

What is claimed is:

1. An implantable port comprising
a base having a passage for receiving an access tube;
a valve assembly in the base, said valve assembly having a bore which receives the access tube and wherein the valve assembly opens in response to movement of the access tube; and
a valve lock having a latch which shifts position to lock the valve assembly open in response to movement of the access tube;
wherein the valve assembly comprises a plunger and wherein the latch comprises a pair of space-filling elements which are displaced by the needle both downwardly, to lower the plunger to open the valve, and outwardly into the receptacle, to lock the plunger open.

2. An implantable port as in claim 1, wherein the valve assembly opens in response to motion of a needle against the plunger.

3. An implantable port as in claim 2, wherein the space-filling elements comprise a pair of balls which are displaced laterally.

4. An implantable port as in claim 1, wherein the valve assembly is selected from the group consisting of pinch valves, sliding valves, slit valves, duckbill valves, and leaflet valves.

5. An implantable port as in claim 1, wherein the bore comprises a tapered bore which seals against the access tube as said tube is inserted therein.

6. An implantable port comprising
a base having a passage for receiving an access tube;
a valve assembly in the base, said valve assembly having a bore which receives the access tube and wherein the valve assembly opens in response to movement of the access tube;
a valve lock having a latch comprising a pair of balls which are displaced laterally into a receptacle and remain in the receptacle to lock the valve assembly open in response to movement of the access tube.

7. An implantable port as in claim 6, wherein the valve assembly opens in response to motion of a needle.

8. An implantable port as in claim 6, wherein the valve assembly comprises a plunger and wherein the pair of balls is displaced both downwardly, to lower the plunger to open the valve, and outwardly into the receptacle, to lock the plunger open.

9. An implantable port as in claim 6, wherein the valve assembly comprises a valve selected from the group consisting of pinch valves, sliding valves, slit valves, duckbill valves, and leaflet valves.

10. An implantable port as in claim 6, wherein the bore comprises a tapered bore which seals against the access tube as said tube is inserted therein.

* * * * *